United States Patent
Matto et al.

(10) Patent No.: US 11,445,956 B2
(45) Date of Patent: Sep. 20, 2022

(54) SYSTEMS AND METHODS FOR BIOBEHAVIORAL-REGULATION TREATMENTS

(71) Applicant: GEORGE MASON UNIVERSITY, Fairfax, VA (US)

(72) Inventors: Holly Christine Matto, Fairfax, VA (US); Padmanabhan Seshaiyer, Fairfax, VA (US)

(73) Assignee: George Mason University, Fairfax, VA (US)

( * ) Notice: Subject to any disclaimer, the term of this patent is extended or adjusted under 35 U.S.C. 154(b) by 77 days.

(21) Appl. No.: 16/376,281

(22) Filed: Apr. 5, 2019

(65) Prior Publication Data

US 2019/0320964 A1 Oct. 24, 2019

Related U.S. Application Data

(60) Provisional application No. 62/653,095, filed on Apr. 5, 2018.

(51) Int. Cl.
*A61B 5/16* (2006.01)
*A61B 5/00* (2006.01)
(Continued)

(52) U.S. Cl.
CPC .......... *A61B 5/165* (2013.01); *A61B 5/0022* (2013.01); *A61B 5/7275* (2013.01); *G06F 3/015* (2013.01);
(Continued)

(58) Field of Classification Search
CPC .......... A61B 2560/0223; A61B 5/0022; A61B 5/165; A61B 5/7275; G06F 2203/011;
(Continued)

(56) References Cited

U.S. PATENT DOCUMENTS

| 2008/0214903 A1* | 9/2008 | Orbach | G06Q 50/22 600/301 |
| 2010/0009324 A1* | 1/2010 | Owens | G16H 20/30 434/236 |

(Continued)

FOREIGN PATENT DOCUMENTS

CN 106214163 B * 12/2019 ............... A61B 5/16

OTHER PUBLICATIONS

Google English translation of CN-106214163-B, accessed Mar. 2022, <https://patents.google.com/patent/CN106214163B/en?oq=cn+106214163B>.*

*Primary Examiner* — Jonathan T Kuo
*Assistant Examiner* — Vynn V Huh
(74) *Attorney, Agent, or Firm* — Morris, Manning & Martin, LLP; Daniel E. Sineway, Esq.

(57) ABSTRACT

Methods and systems for recovery-adaptive biobehavioral-regulation treatments for relapse. In various embodiments, a user wears a sensor that collects biobehavioral data regarding the user and is operatively connected to an electronic computing device associated with the user. Generally, the disclosed system monitors the collected biobehavioral data to mitigate relapse of a previous disease and/or disorder (e.g., addiction, depression, post-traumatic stress disorder, etc.) by presenting personalized recovery cues (e.g., images, videos, etc.) to the user when the user is experiencing stimuli that increase the risk of relapse. In addition, the user has the ability to modulate the implicated brain structure image interactively on the smartphone interface (e.g., changing the size, texture, color, image), in order to change its functionality in real-time and improve in-the-moment emotional regulation. By presenting the personalized recovery cues, in various embodiments, the risk of relapse in the user can be reduced.

16 Claims, 4 Drawing Sheets

EXEMPLARY USER REGISTRATION / TREATMENT CALIBRATION PROCESS

(51) Int. Cl.
  *G06F 3/01*   (2006.01)
  *G16H 20/10*  (2018.01)
  *G16H 40/63*  (2018.01)
  *G16H 50/20*  (2018.01)
  *G16H 50/30*  (2018.01)
  *G16H 50/50*  (2018.01)
  *G16H 50/70*  (2018.01)

(52) U.S. Cl.
  CPC . *A61B 2560/0223* (2013.01); *G06F 2203/011* (2013.01)

(58) Field of Classification Search
  CPC ........ G06F 3/015; G16H 20/10; G16H 40/63; G16H 50/20; G16H 50/30; G16H 50/50; G16H 50/70
  See application file for complete search history.

(56) References Cited

U.S. PATENT DOCUMENTS

| | | | | |
|---|---|---|---|---|
| 2014/0200432 A1* | 7/2014 | Banerji | ................ | A61H 99/00 600/383 |
| 2017/0224273 A1* | 8/2017 | Vardas | ............... | A61B 5/02405 |

\* cited by examiner

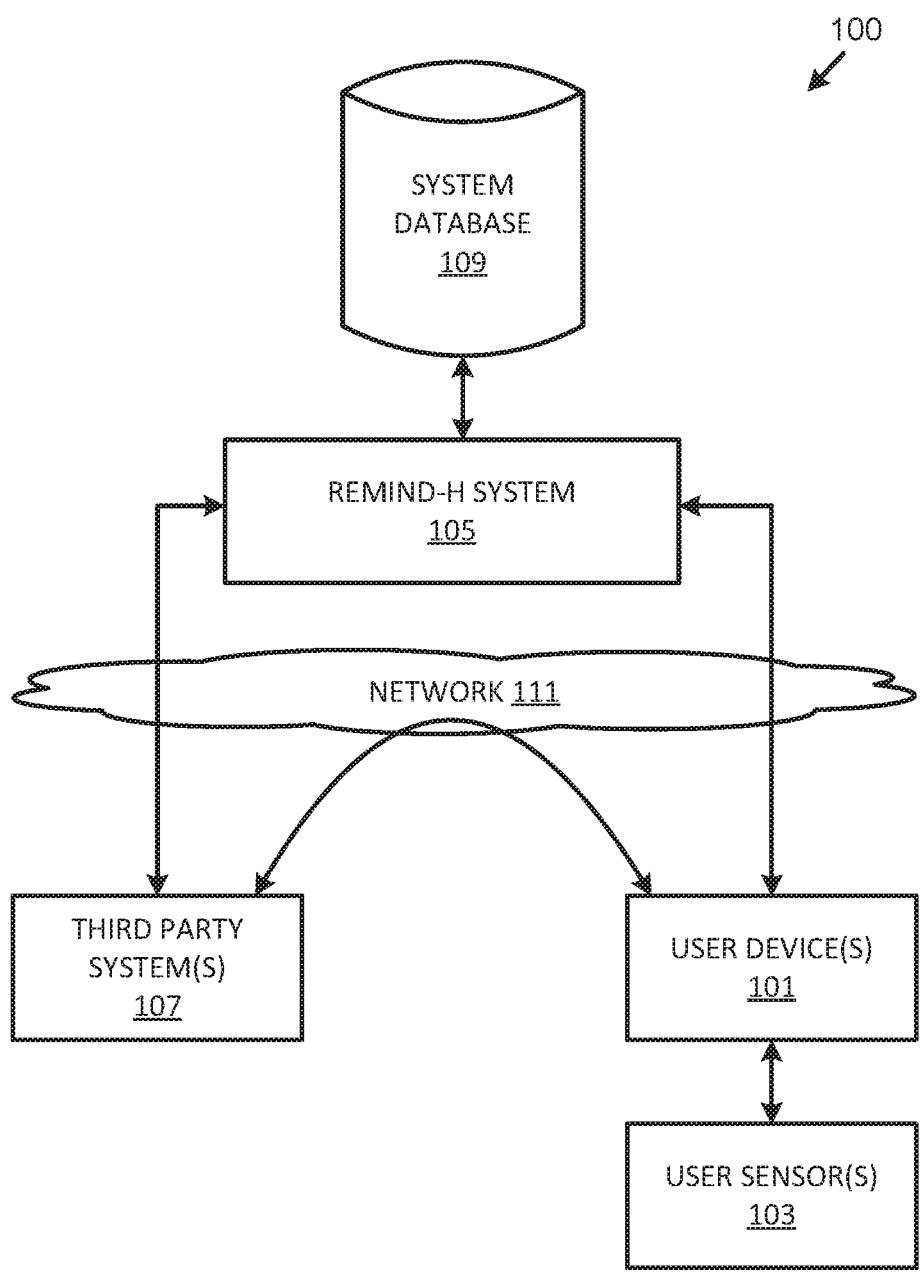
FIG 1: EXEMPLARY SYSTEM ARCHITECTURE

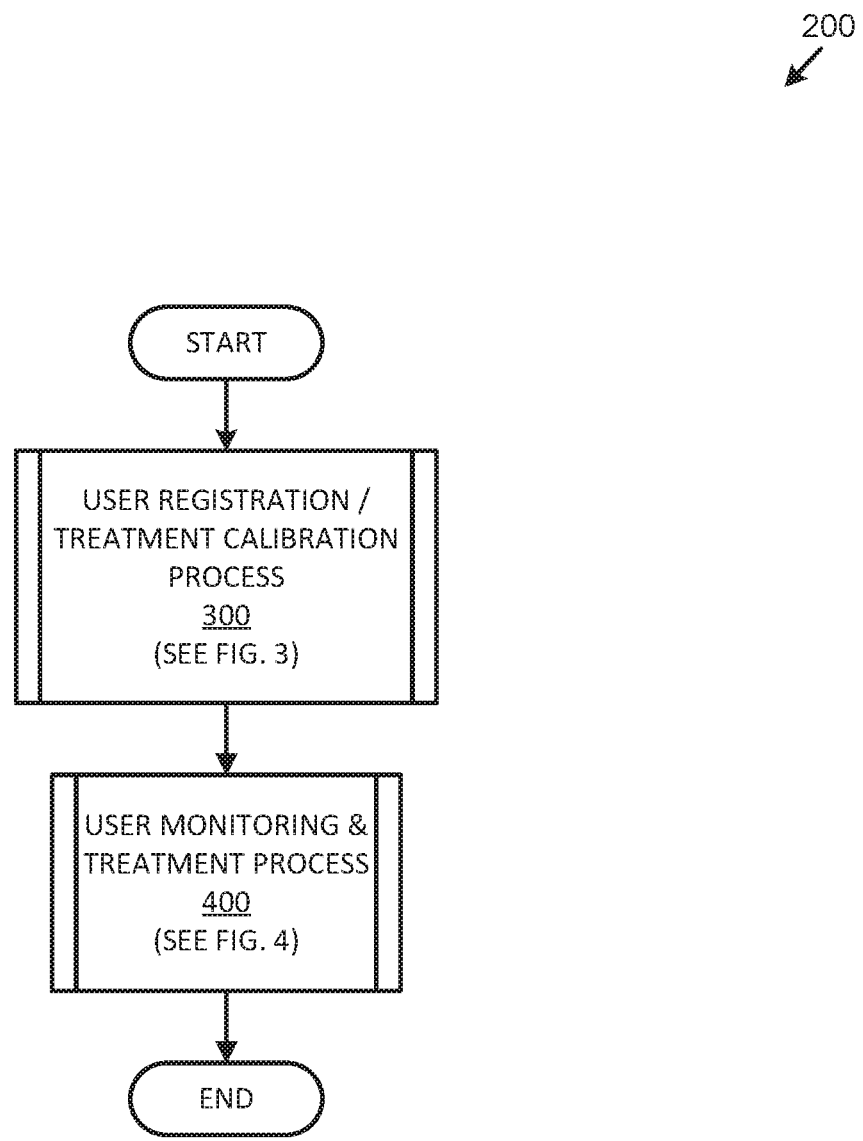
FIG 2: EXEMPLARY SYSTEM PROCESS

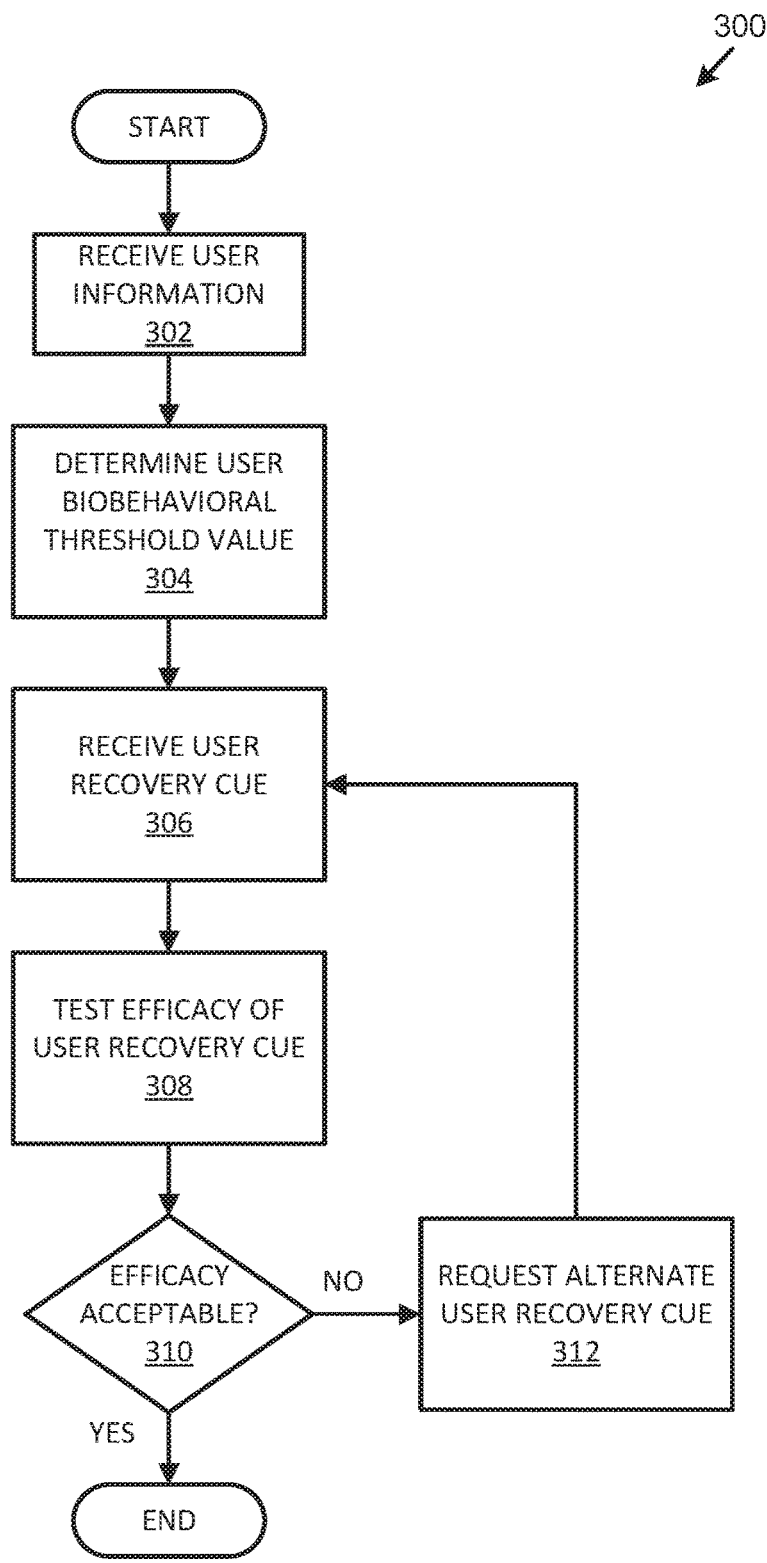
FIG 3: EXEMPLARY USER REGISTRATION / TREATMENT CALIBRATION PROCESS

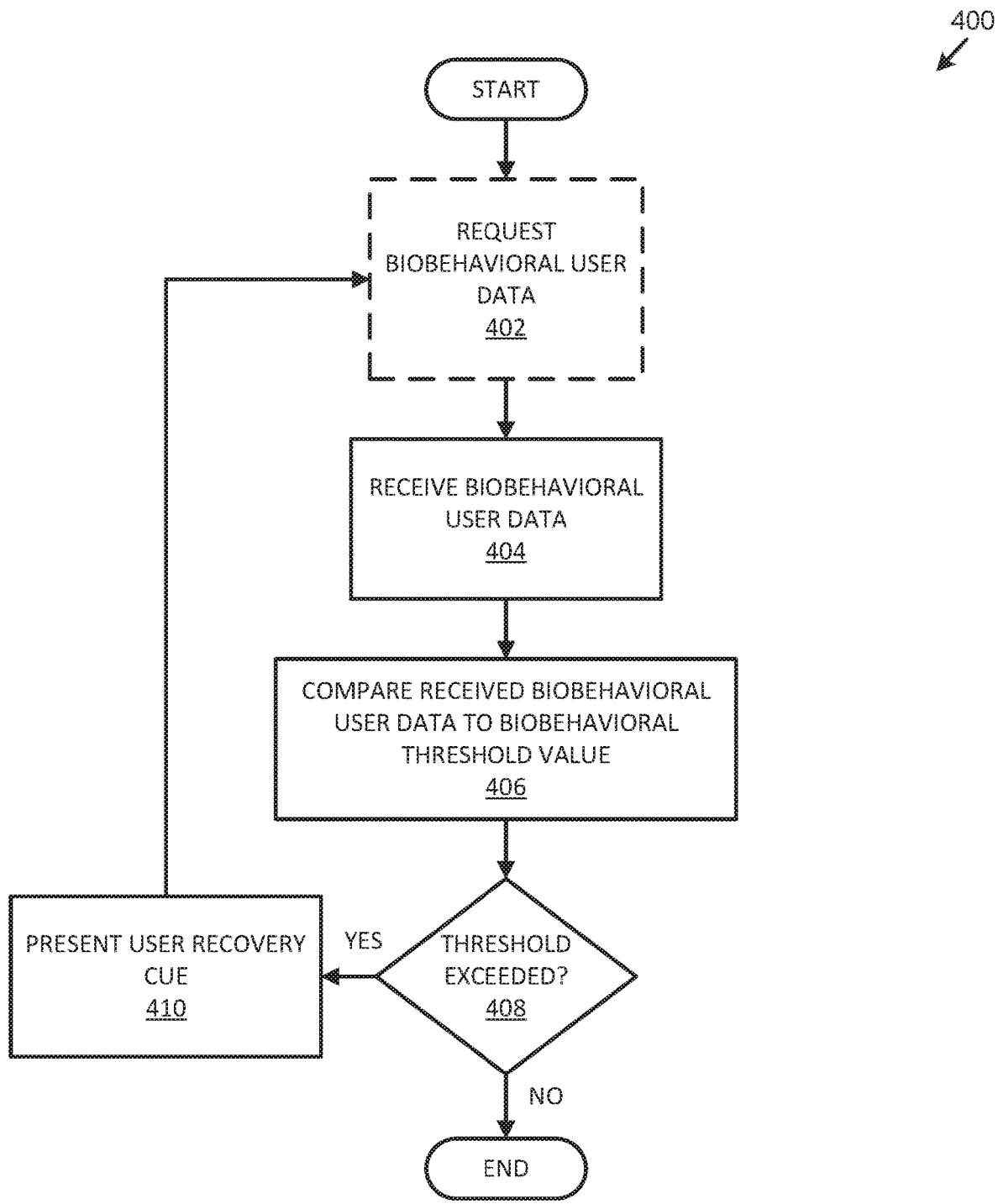
FIG 4: EXEMPLARY USER MONITORING & TREATMENT PROCESS

SYSTEMS AND METHODS FOR BIOBEHAVIORAL-REGULATION TREATMENTS

CROSS-REFERENCE TO RELATED APPLICATION

This application claims the benefit of and priority to U.S. Provisional Patent Application No. 62/653,095, entitled "Systems and Methods for Biobehavioral-Regulation Treatments," filed Apr. 5, 2018, the disclosure of which is hereby incorporated by reference herein in its entirety.

TECHNICAL FIELD

The present methods and systems generally relate to recovery-adaptive biobehavioral-regulation treatments for diseases and/or disorders to mitigate relapses and/or symptoms. More particularly, the methods and systems relate to software and electronic computing devices that can monitor the biobehavioral data of the user to mitigate relapses of a disease and/or disorder by presenting personalized recovery cues to the user when the user is experiencing stimuli that increase the risk of relapse.

BACKGROUND

It is well-documented that individuals who reenter their communities after inpatient drug treatment experience high relapse rates, particularly in the first 3 to 6 months (i.e., 40%-60% will relapse in first year). For example, studies have found that 60% of heroin users will relapse within 3 months of treatment, and 75% will relapse within 12 months. One reason relapse occurs is that individuals are immediately exposed to environmental stimuli related to their prior drug use (e.g., people, places, activities, or things that are reminders of drug use). These external cues trigger internal reactions—such as emotions, cognitions, and negative mood states—that increase drug-urge intensity and heighten drug-use risk. Actual drug use is caused by increased craving/drug-use urge; exposure to drug cues increases craving and the urge to use drugs. Risk factors for continued posttreatment to alcohol use include both craving and stress, with an implicit attention bias that is specific to visual drug-related cues. The mesocorticolimbic sensitization theory of addiction and relapse posits that, over time, drug cues become charged with the same motivation-inducing state as the drug itself, and negative emotions and stress can magnify drug-cue priming effects. Urge for the drug occurs as exposure to cues increase dopamine in the reward circuitry of the brain, particularly along the pathway from the ventral tegmental area to the nucleus accumbens, leading to dysregulation in the reward system and motivating drug-seeking behavior. At least one review of the neurobiological mechanisms of addiction suggested that it is dysregulation in the stress and reward systems that lead to relapse vulnerability. For example, because drug-cue associations are thought to be mediated by dopamine projections to the mesolimbic area—which leads to cue reactivity—at least one study used cognitive-bias modification training to target cue reactivity in the nucleus accumbens and amygdala, with fMRI results showing reactivity reductions posttraining.

These neurobiological studies suggest that addiction is chronic and progressive, changing in its expression from impulsivity (driven by positive reinforcement) to compulsivity (driven by negative reinforcement, or seeking "relief" from aversive experiences). Mesolimbic dopamine dysregulation accounts for the changes in reward system responsivity and diminishes the pleasure of naturally rewarding stimuli. Over time, reward system thresholds change, compelling greater substance use. In addition to dysregulation of the reward system, chronic substance use engages the body's stress response system, creating negative affective states. Negative affect results from both decreased reward-system activity and increased activity in the extended amygdala.

Although environmental aspects such as people, places, and things can be controlled to an extent—for example, by avoiding friends who use drugs or transitioning directly to a recovery house—drug-related cue exposure will naturally and inevitably occur at some point as clients return to their pretreatment community spaces. Although cognitive-oriented relapse prevention strategies are widely used in inpatient treatment settings, when an individual is confronted with environmentally trigged drug cues in real time (i.e., at the point of being exposed to the cue in community settings), they have little success calling to mind and effectively using cognitive-oriented relapse prevention strategies because cue processing and reactivity operates at a cognitively unconscious or implicit level of awareness. Cognitive control resources (e.g., cognitive behavioral therapy) have been shown to exert minimal to modest impact on behavioral decision-making in the presence of intense affective material. In fact, implicit drug-related triggers provide a powerful explanation for drug addiction, with a considerable amount of research showing that people will continue to use drugs when returning to cue-saturated environments, contributing to significant posttreatment drug-use relapse rates. Tools are needed to detect this implicit cue reactivity in real-time—that is, at the point of exposure to the cue—and to use individually tailored intervention strategies to help individuals to recognize and resist the stimuli, thereby reducing drug urge and preventing drug use. Research has sparsely focused on preventing relapses from occurring in the first place (i.e., relapse-adaptive).

Therefore, there is a long-felt but unresolved need for methods and systems that are recovery-adaptive rather than relapse-reactive to promote recovery and decrease the relapse risk.

SUMMARY

Disclosed herein are methods and systems for providing a recovery support for users that monitors their biobehavioral state and strategically delivers, in real-time, personalized recovery cues to treat/prevent relapse. In one specific embodiment, the method can include: measuring one or more baselines of biobehavioral data of a user with one or more sensors; calibrating one or more behavioral risk thresholds of the user using the one or more sensors to measure a deviation from the one or more baselines of biobehavioral data of the user; creating a cache of one or more recovery cues of a user; collecting one or more real-time biobehavioral data of the user with one or more sensors; and if the one or more real-time biobehavioral data exceeds the threshold behavioral risk threshold of the user, providing the one or more recovery cues to a device of the user.

In another specific embodiment, the method can include a computer-readable medium that can include instructions that, when executed by a computer, cause the computer to: measure one or more baselines of biobehavioral data of a user with one or more sensors; calibrate one or more behavioral risk thresholds of the user using the one or more sensors to measure a deviation from the one or more baselines of biobehavioral data of the user; create a cache of one or more recovery cues of a user; collect one or more real-time biobehavioral data of the user with one or more sensors; and if the one or more real-time biobehavioral data exceeds a threshold of the one or more baselines of biobehavioral data of the user, providing the one or more recovery cues to an electronic computing device of the user.

In another specific embodiment, the system can include: one or more sensors; one or more electronic computing devices; and a server, wherein the server can include: one or more processors, and a memory comprising instructions that, when executed by the one or more processors, cause the one or more processors to: measure one or more baselines of biobehavioral data of a user with one or more sensors; calibrate one or more behavioral risk thresholds of the user using the one or more sensors to measure a deviation from the one or more baselines of biobehavioral data of the user; create a cache of one or more recovery cues of a user; if the one or more real-time biobehavioral data exceeds a threshold of the one or more baselines of biobehavioral data of the user, providing the one or more recovery cues to an electronic computing device of the user.

BRIEF DESCRIPTION OF DRAWINGS

So that the manner in which the above recited features of the present invention can be understood in detail, a more particular description of the invention, briefly summarized above, can be had by reference to embodiments, some of which are illustrated in the appended drawings. It is to be noted, however, that the appended drawings illustrate only typical embodiments of this invention and are therefore not to be considered limiting of its scope, for the invention can admit to other equally effective embodiments FIG. 1 illustrates an exemplary system architecture, according to one embodiment of the present disclosure.

FIG. 2 is a flowchart showing an exemplary system process, according to one embodiment of the present disclosure.

FIG. 3 is a flowchart showing an exemplary user registration/treatment calibration process, according to one embodiment of the present disclosure.

FIG. 4 is a flowchart showing an exemplary user monitoring and treatment process, according to one embodiment of the present disclosure.

DETAILED DESCRIPTION

Methods and systems for software and devices, tailored to a patient-specific diagnosis with programmable neurophysiological behavioral risk set-points can be a useful tool in helping individuals monitor symptomology. When connected to a personalized mobile intervention on a smartwatch or smartphone or other personal computing device, activated when the electronic computing device detects heightened risk, there is an opportunity for in-real time symptom management that is particularly useful to patients discharging from hospital care who are at risk of exposure to triggering experiences in their environment.

The methods and systems can harness the power of the recovering brain by providing a mobile device recovery support system for users that monitors their biobehavioral state and strategically delivers, in real-time, personalized recovery cues to treat/prevent relapse. Prior to leaving treatment (for a particular disease, disorder, etc.), the user establishes, in one embodiment with help from his/her treating practitioner, baseline biobehavioral measurements and creates a cache of his/her own recovery cue images—images, videos, interactive multimedia, sober support contacts, audio recordings (e.g., songs/music/sounds), etc.—for later presentation to the user. Generally, the user wears a sensor that collects biobehavioral data regarding the user in real time (e.g., heart rate variability, pulse, respiratory rate, etc.). Utilizing personal motivations to help users stay connected with their recovery goals, the disclosed system displays a recovery cue when the collected biobehavioral data hits a specified threshold (e.g., indicating that the user is encountering a situation that places the individual at high risk for relapse). In addition, the user has the ability to modulate the implicated brain structure image interactively on the smartphone (or other mobile/wearable device) interface (e.g., changing the size, texture, color, image), in order to change its functionality in real-time and improve in-themoment emotional regulation.

By identifying the reactivity of a user on an implicit level and initiating treatment proactively, the disclosed system generally changes the entire paradigm of network support from a process initiated by the user (e.g., "relapse reactive") to one that is automatically received in physiologically-activated moment of need (e.g., "recovery adaptive").

Such methods and systems can offer both passive and interactive intervention features. Passive recovery cue exposure can activate the pre-programmed cues on a smartwatch or other screen and adjust the frequency of exposure (dosage) presentation according to the physiological data monitoring by the sensor, and interactive features can allow a person to interactively change the sensory characteristics of the image on the screen (e.g, color, visualized texture, tactile sensation such as vibration, size, and shape), using a pop-up menu of regulation selections.

The system can permit users to connect with the larger user community of the system for additional recovery support—providing an immediate support system, as well as an opportunity to share success stories. Further, because the device, in one embodiment, constantly records biobehavioral data as well as time and location data, the user and his/her treating practitioner may accurately identify when and where the user encountered relapse risks over a preceding period of time (e.g., days, weeks, etc.) for further personalization of a user's treatment.

Diseases and/or disorders that can be treated using the present methods and systems can include, but are not limited to, addiction disorders, such as substance addiction, depression, post-traumatic stress disorder, anxiety disorders, phobias, and other behavioral regulation disorders.

For the purpose of promoting an understanding of the principles of the present disclosure, reference will now be made to the embodiments illustrated in the drawings and specific language will be used to describe the same. It will, nevertheless, be understood that no limitation of the scope of the disclosure is thereby intended; any alterations and further modifications of the described or illustrated embodiments, and any further applications of the principles of the disclosure as illustrated therein are contemplated as would normally occur to one skilled in the art to which the disclosure relates. All limitations of scope should be determined in accordance with and as expressed in the claims.

For the purposes of example and explanation of the fundamental processes and components of the disclosed systems and methods, reference is made to FIG. 1, which illustrates an exemplary architecture 100 of one embodiment of the present disclosure. As will be understood and appreciated, the exemplary architecture 100 shown in FIG. 1 represents merely one approach or embodiment of the present system, and other aspects are used according to various embodiments of the present system Referring to FIG. 1, the user device 101 can be operatively connected to a user sensor 103, recovery cue delivery system 105 (also referred to as the "Recovery Engaged Mind-health" or "REMind-h"), and a third party system 107 via a network 111 to monitor biobehavioral data regarding a user to prevent relapse of a previous condition/disease/disorder by presenting personalized recovery cues to the user when the user is experiencing stimuli that increase the risk of relapse. By presenting the personalized recovery cues, the risk of relapse is reduced.

The biobehavioral data of the user that can be collected regarding the user can include, but are not limited to, heart rate, respiratory rate, brain activity, body temperature, electrodermal response, blood oxygenation, and muscle movement.

The biobehavioral data can be collected continuously or at predetermined intervals, every thirty seconds, every minute, every five minutes, every half hour, every hour, etc.; at random intervals; when requested by a user; when requested by a practitioner; etc.).

The personalized recovery cues that can be presented to the user can include, but are not limited to, tactile sensations, auditory sounds, scents, messages, music, personalized supportive voices, visual stimuli, images, and photographs. Music and visual imagery are processed in the brain at both implicit and explicit levels of awareness and offer a holistic "whole brain" intervention strategy. For example, personalized music stimulates memories connected to positive feelings and reduces agitation; music has also been shown to enhance cognitive functioning and emotional adjustment for patients with brain injuries. Similarly, art and visual imagery have been found to change the brain in ways that improve attention, memory, and concentration in populations with cognitive impairments.

For example, a user can encounter a situation that increases his/her relapse risk (e.g., being offered drugs, running into friends with whom the recovering drug addict may have done drugs previously, etc.). The user sensor 103 detects, in various embodiments, biobehavioral data regarding the user, which is compared, by either the user device 101 or the REMind-h system 105, to a behavioral risk threshold value to determine whether the situation is having a physiological impact on the user. If the data does not exceed the threshold value, then, in one embodiment, no further action is taken. If the data exceeds the threshold, then, in one embodiment, the REMind-h system 105 instructs the user device 101 to display personalized recovery cues (also referred to herein as "treatment") to the user.

A user device(s) 101 can be electronic computing device that is capable of performing the functionality disclosed herein. For example, the device can include, but is not limited to, desktop computer, laptop computer, tablet computer, smartphone, smartwatch, wearable electronic device, etc. In various embodiments, the user device 101 communicates via network 111 with the user sensor(s) 103, the REMind-h system 105, and the third party system 107 to conduct the processes disclosed herein. In one embodiment, the user device 101 is the device through which the biobehavioral data regarding the user is compared to the threshold value or is transmitted to the REMind-h system 105 for comparison to the threshold value. In one embodiment, the user device 101 has an output device (e.g., display, speaker, etc.) and presents the recovery cue to the user. In various embodiments, a single user may use a single user device 101 or multiple user devices 101.

The user sensor(s) 103 are any device that is capable of performing the functionality disclosed herein. For example, the user sensor(s) 103 can include, but is not limited to, pulse monitor, thermometer, electrode, pulse oximeter, glucose meter, etc. The user sensor 103 can communicate via a network 111 with the user device 101 to conduct the processes disclosed herein. The user sensor 103 can collect biobehavioral data regarding the user and transmits it to the user device 101. In various embodiments, a single user may be monitored by a single user sensor 103 or multiple user sensors 103 (each collecting the same or different biobehavioral data). In one embodiment, the user device(s) 101 can include the user sensor(s) 103 (e.g., smartwatch integrated with a pulse monitor, etc.) such that communication via network 111 between the user device(s) 101 and the user sensor(s) 103 is unnecessary.

The REMind-h system 105 can be any computing device (e.g., desktop computer, laptop, servers, tablets, etc.), combination of computing devices, software, hardware, or combination of software and hardware that is capable of performing the functionality disclosed herein. The REMind-h system 105 can include, but is not limited to a desktop computer, laptop, servers, and tablets. In various embodiments, the REMind-h system 105 is operatively connected to the user device(s) 101 and the third party system(s) 107 via the network 111 to conduct the processes disclosed herein. In one embodiment, the REMind-h system 105 receives biobehavioral data from the user device 101 and determines whether to present recover cues to the user by comparing the received biobehavioral data to a predetermined threshold value. The REMind-H system 105 may also send instructions to the user device 101 to present the recovery cue. In one specific embodiment, the instructions can include the recovery cue.

The REMind-h system 105 can further include a system database 109. The system database 109 may be any computing device. For example, the REMind-h system 105 can include, but is not limited to, desktop computers, laptops, servers, tablets, or any combination of computing devices, software, hardware, combination of software and hardware, database (e.g., stored in the cloud or on premise, structured as relational, etc.), or combination of databases that is capable of performing the functionality disclosed herein. In one embodiment, the system database 109 can be local to the REMind-h system 105. For example, the REMind-h system 105 can include the system database 109. In other embodiments, the system database 109 is virtual or stored in a remote environment (e.g., in the "cloud"). In one specific embodiment, the system database 109 can store recovery cues and threshold values corresponding to the users.

A third party system 107 can be any computing device. For example, the third party system 107 can include, but is not limited to, desktop computers, laptops, servers, tablets combination of computing devices, software, hardware, or combination of software and hardware that is capable of performing the functionality disclosed herein. The third party system 107 can communicate via a network 111 with the user device 101 and the REMind-h system 105 to conduct the processes disclosed herein. In one specific embodiment, the third party system 107 can include the personalized recovery cues and provides them to the user device 101 and/or the REMind-h system 105. In another specific embodiment, the third party system 107 can include medical records regarding the user and provides them to the REMind-h system 105.

The network 111 can be any connection capable of transferring data between two or more computer systems.

For example, the network 111 secure or unsecured connections, Bluetooth, wireless or wired local-area networks (LANs), cell network, and the Internet.

Referring to FIG. 2, an exemplary system process 200 is shown according to one embodiment of the present disclosure. The steps and processes shown in FIG. 2 (and those of all other flowcharts and sequence diagrams shown and described herein) can operate concurrently and continuously, are generally asynchronous and independent, and are not necessarily performed in the order shown. The exemplary system process 200 can include the process by which the present disclosure registers users, calibrates treatments for those users, and monitors/presents treatments to those users.

The exemplary system process 200 can begin with the user registration/treatment calibration process 300 (further details of which will be discussed in association with the description of FIG. 3) in which the user is registered with the system and the recovery cues of the user are calibrated to determine their efficacy. After the process 300, the user monitoring and treatment process 400 can occur (further details of which will be discussed in association with the description of FIG. 4), wherein the user is monitored and treatment is provided as appropriate.

The system process 200 can use virtual reality (VR) technology to calibrate patient-specific behavioral risk and recovery-regulation set-points for the user registration/treatment calibration process 300. VR technology can be used to simulate patient-specific trauma—related or otherwise distressing cue-triggering experiences that allows for calibration of a personalized neurophysiological risk-reactivity set-point, captured in-session using neurophysiological sensors worn during the scenario. In addition, simulation of a recovery-regulation experience using patient-specific virtually-generated supportive relationships, trauma recovery-enhanced environmental conditions, and trauma recovery-associated sensory cues, could allow for the calibration of a recovery-regulated neurophysiological set-point, captured by the same in-session neurophysiological sensor systems. Over time, the device could calibrate a neurophysiological recovery profile based on activation and non-use patterning.

Referring to FIG. 3, an exemplary user registration/treatment calibration process 300 is shown according to one embodiment of the present disclosure. The exemplary registration/treatment calibration process 300 can include the process by which the user is registered with the system and the recovery cues of the user are calibrated to determine their efficacy.

In various embodiments, the process 300 begins at step 302, wherein the system (e.g., REMind-h system 105 from FIG. 1) receives user information regarding the user (e.g., demographic data, contact information, etc.). In one specific embodiment, the user information is input using the user device 101. The system registers the user based on the user information. At step 304, in various embodiments, the system determines the biometric threshold value of the user. This threshold value can include the value that indicates whether the user is currently experiencing a situation that suggests a relapse risk. In one specific embodiment, the threshold value can be determined by measuring the biobehavioral data of the user in a predetermined situation that does not present a relapse risk (e.g., doctor's office, calm situation, quiet situation, etc.). For example, if the system is monitoring a user's heart rate, a heart rate variability threshold/score (e.g., a measure of the variation of heartbeats within a specific timeframe) can be established such that exceeding that threshold indicates presentation of a relapse risk is appropriate (e.g., as would occur when a user's pulse speeds up, when in a relapse-inducing situation). This disclosure places no limitations on the type of threshold that may be used by the system and/or device. In various embodiments, instead of a single threshold, the threshold represents a series of rules that are satisfied (e.g., is the user's heart rate variability above a particular level; if yes, has the user's heart rate variability changed faster than a particular rate; etc.).

At step 306, in one specific embodiment, the system can receive (or generate) the personalized recovery cues of the user—these recovery cues can include any stimulus specifically-tailored to the user to remind the user of the recovery process and prevent relapse (e.g., images/photos of special hobbies, nature scenes, meaningful individuals/animals, important places, supportive statements, etc.; audio recordings of meditations, nature sounds, music, etc.; interactive automated chat; etc.). The user can provide one or more personalized recovery cues that are retrieved from the user device 101 and/or the third party system 107 (and are tested for their efficacy at step 308). In one specific embodiment, the REMind-h system 105 can retrieve one or more generic recovery cues from the system database 109 and/or the third party system 107 (and are tested for their efficacy at step 308 to personalize them to the user, selecting only those recovery cues that are effective). At step 308, the system can test the efficacy of the received recovery cues by collecting biobehavioral data regarding the user while introducing the user to a relapse-inducing situation (e.g., showing drug paraphernalia to a recover drug addict, etc.) and then presenting the recovery cue. At step 310, the system can determine whether the efficacy of recovery cue is acceptable by analyzing the collected biobehavioral data and comparing it to the predetermined threshold values (e.g., to determine whether the recovery cue reduces the heart rate variability of the user below the predetermined threshold values, etc.). If the efficacy of the recovery cue is unacceptable, then at step 312, the system requests additional recovery cues and returns to step 306. If, however, the efficacy of the recovery cue is acceptable, then the process 300 ends thereafter.

Referring to FIG. 4, an exemplary user monitoring and treatment process 400 is shown according to one embodiment of the present disclosure. The exemplary user monitoring and treatment process 400 can include the process by which the user is monitored for relapse risk and treatment is provided as appropriate. In one specific embodiment, the process 400 can occur continuously (e.g., steps 402-410 repeat) so that the user is constantly monitored. In another specific embodiment, the process 400 occurs at a predetermined interval (e.g., every minute, every five minutes, etc.) so that the user receives adequate monitoring.

In various embodiments, the process 400 begins at step 402, wherein the system optionally requests biobehavioral data from the user device and/or user sensor (e.g., user device 101 or user sensor 103 from FIG. 1). In other embodiments, rather than requesting the data, the user device 101 "pushes" the data at periodic intervals or based on a triggering event (e.g., data exceeding a certain threshold), such that data does not need to be specifically requested at step 402. Generally, at step 404, the system receives the requested biobehavioral data. Thus, at step 406, the system compares the received biobehavioral data to the threshold value to determine whether to present the recovery cue to the user (e.g., by calculating the user's heart rate variability and comparing the calculated value to the threshold, etc.). If the threshold is exceeded, as determined at step 408, then the user recovery cue is presented to the user at step 410 (e.g., the system sends instructions to the user device 101 to present the recovery cue and/or sends the recovery cue to the user device 101 for presentation). In one specific embodiment, the specific recovery cue presented at step 410 may be dependent on how far away from the threshold the biobehavioral data is (e.g., the user may have different recovery cues with different efficacies designed to have increased impacts on the user, depending on the situation).

In one embodiment, the system may record information, at step 410, regarding the effect of the recovery cue so that the treatment may be optimized at a later time (e.g., removing less-effective recovery cues, prioritizing more-effective recovery cues, etc.). In various embodiments, the system may use one or more machine learning algorithms to evaluate and update the efficacy of the recovery cues at step 410. Generally, if the threshold value is not exceeded, then the process 400 ends thereafter.

Examples

In order to provide a better understanding of the foregoing discussion, the following non-limiting examples are offered. Although the examples can be directed to specific embodiments, they are not to be viewed as limiting the invention in any specific respect.

An experiment was conducted on the disclosed system to examine the effect of personalized recovery cues on reducing drug cue exposure reactivity, as measured by change in heart rate variability (also referred to as "HRV"), in a sample of young adults in substance use recovery. Participants were recruited through the campus wellness office of George Mason University. A total of 8 young adults (4 male; 4 female) in substance use recovery participated in the study. Participants took part in two individual interviews. The first interview asked open-ended questions about their drug cue triggers and requested that they come to the second interview with a compilation of their recovery-specific images, music, sounds, inspirational quotes, etc. that were associated with their commitment to recovery (e.g., recovery cues). In the second interview, each participant's HRV was measured at baseline, just after exposure to their drug-related stimuli (pictures of their specific drug cue triggers, as determined in the first interview), and immediately after exposure to the specific recovery cue that the participant brought to the second interview.

In various embodiments, participants' alcohol and drug-cue triggers comprised the following examples: pictures of red wine or being alone at a bar; being alone with one's own thoughts; and family themes. Generally, stress and isolation were perceived as the biggest triggers. In contrast, in various embodiments, participants' personalized recovery cues included: images/photos of special hobbies, nature scenes such as waterfalls, meaningful relationships and/or important places, text message of supportive statements from a therapist, inspirational quotes (e.g., ALCOHOLICS ANONYMOUS® (also referred to as "AA") serenity prayer, "accept what is, let go of what was," "breathe in deeply to bring your mind home to your body," "face it, accept it, deal with it, then let it go"), favorite pet, the 12 steps, and important people (e.g., an AA sponsor); and audio clips of meditations, nature sounds, songs/music that were healing or otherwise had significant meaning to participants.

HRV, which is a measure of autonomic regulation of the heart, was selected in this embodiment as the neurophysiological outcome measure because neurocardiac signaling generally influences cognitive-affective processes that lead to relapse. The heart and brain are in reciprocal communication, and bodily reactions affect neural response and behavioral functioning simultaneously. HRV measures the variation in heart beat intervals that is influenced by sympathetic nervous system (also referred to as "SNS") and parasympathetic nervous system (also referred to as "PNS") input to the sino-atrial node of the heart. HRV generally measures the time gap between individual heart beats while the body is resting. For example, when the body inhales, the heart speeds up, and when the body exhales, the heart slows down; this difference in heart rate is captured by HRV. The SNS raises the heart rate and blood pressure, which increases an individual's muscle power and speed. The PNS helps with recovery and relaxation of muscles and, hence, slows the heart rate and lowers blood pressure. Therefore, increased PNS activity increases HRV, whereas increased SNS activity decreases HRV. Studies have generally found that aspects of shift-and-persist strategies, such as flexible coping, emotion regulation, and benefit finding, are associated with greater heart rate variability.

An HRV score, in various embodiments, was calculated for each participant by the root mean square of the successive differences (also referred to as "rMSSD") in heart rate, which reflects the integrity of vagus nerve-mediated autonomic control of the heart—with higher numbers indicating a more relaxed state. Table 1 below gives the HRV score for each of the 8 participants after presentation of their drug cue and then after presentation or their personalized recovery cue.

TABLE 1

HRV Score Exemplary Pilot Study Participants

| Participant | Drug Cue | Recovery Cue (Shown Immediately after Drug Cue) |
| --- | --- | --- |
| 1 | 41.4 | 45.8 |
| 2 | 39.8 | 30.8 |
| 3 | 82.3 | 102.4 |
| 4 | 21.5 | 51.9 |
| 5 | 67.2 | 69.0 |
| 6 | 31.2 | 92.5 |
| 7 | 109.3 | 139.3 |
| 8 | 35.7 | 43.5 |

The exemplary results show a pattern of increased HRV Score when participants were exposed to their recovery cues after being exposed to drug cues (simulating being displayed their recovery cue when the system detects increased HRV from being in a relapse-inducing situation). The exemplary results generally showed that a participant's recovery cue was associated with a more relaxed physiological state as compared to immediately after drug cue exposure (HRV Score Mean=53.55 as compared to HRV Score Mean=71.90; $P<=0.05$). Participant 2 was the only one who did not have a personalized recovery cue, so stock library images of pleasing nature scenes were used as recovery cues. Participant 2's HRV score reinforces the importance of personalization of the recovery cue because, in one embodiment, the non-personalized recovery cue did not show the same HRV regulating trend as the personalized recovery cues of the other participants.

The example suggests that it is not just objectively pleasant cues (e.g., nature scenes, babies' faces, etc.) that are effective per se, but the personalization and collection of meaningful positive recovery-related cues that are influential, at least in the measured embodiment. In one embodiment, audio-based recovery cues will be very powerful for some users (e.g., Participate 1). Moreover, in various embodiments, a user's time in recovery will likely influence the individual's reactivity to recovery cues. Also, in various embodiments, a visual dynamic (e.g., moving) graphic that includes colors and shapes and that corresponds to a pre-selected healing music pattern would allow for a visually translated audio experience without sound, which would permit the benefits of healing music to be incorporated in a visual, non-distractive, way for users.

From the foregoing, it will be understood that various aspects of the processes described herein are software processes that execute on computer systems that form parts of the system. Accordingly, it will be understood that various embodiments of the system described herein are generally implemented as specially-configured computers including various computer hardware components and, in many cases, significant additional features as compared to conventional or known computers, processes, or the like, as discussed in greater detail herein. Embodiments within the scope of the present disclosure also include computer-readable media for carrying or having computer-executable instructions or data structures stored thereon. Such computer-readable media can be any available media which can be accessed by a computer, or downloadable through communication networks. By way of example, and not limitation, such computer-readable media can comprise various forms of data storage devices or media such as RAM, ROM, flash memory, EEPROM, CD-ROM, DVD, or other optical disk storage, magnetic disk storage, solid state drives (SSDs) or other data storage devices, any type of removable nonvolatile memories such as secure digital (SD), flash memory, memory stick, etc., or any other medium which can be used to carry or store computer program code in the form of computer-executable instructions or data structures and which can be accessed by a computer.

When information is transferred or provided over a network or another communications connection (either hardwired, wireless, or a combination of hardwired or wireless) to a computer, the computer properly views the connection as a computer-readable medium. Thus, any such a connection is properly termed and considered a computer-readable medium. Combinations of the above should also be included within the scope of computer-readable media. Computer-executable instructions comprise, for example, instructions and data which cause a computer to perform one specific function or a group of functions.

The above-described features and applications can be implemented as software processes that are specified as a set of instructions recorded on a computer readable storage medium (also referred to as computer readable medium). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

In this specification, the term "software" is meant to include firmware residing in read-only memory or applications stored in magnetic storage or flash storage, for example, a solid-state drive, which can be read into memory for processing by a processor. Also, in some implementations, multiple software technologies can be implemented as sub-parts of a larger program while remaining distinct software technologies. In some implementations, multiple software technologies can also be implemented as separate programs. Finally, any combination of separate programs that together implement a software technology described here is within the scope of the subject technology. In some implementations, the software programs, when installed to operate on one or more electronic systems, define one or more specific machine implementations that execute and perform the operations of the software programs.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

These functions described above can be implemented in digital electronic circuitry, in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, for example microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic or solid state hard drives, read-only and recordable BLU-RAY® discs, ultra-density optical discs, any other optical or magnetic media, and floppy disks. The computer-readable media can store a computer program that is executable by at least one processing unit and includes sets of instructions for performing various operations. Examples of computer programs or computer code include machine code, for example is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, for example application specific integrated circuits (ASICs) or field programmable gate arrays (FPGAs). In some implementations, such integrated circuits execute instructions that are stored on the circuit itself.

As used in this specification and any claims of this application, the terms "computer", "server", "processor", and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some aspects of the disclosed subject matter, a server transmits data (e.g., an HTML page) to a client device (e.g., for purposes of displaying data to and receiving user input from a user interacting with the client device). Data generated at the client device (e.g., a result of the user interaction) can be received from the client device at the server.

It is understood that any specific order or hierarchy of steps in the processes disclosed is an illustration of example approaches. Based upon design preferences, it is understood that the specific order or hierarchy of steps in the processes may be rearranged, or that all illustrated steps be performed. Some of the steps may be performed simultaneously. For example, in certain circumstances, multitasking and parallel processing may be advantageous. Moreover, the separation of various system components illustrated above should not be understood as requiring such separation, and it should be understood that the described program components and systems can generally be integrated together in a single software product or packaged into multiple software products.

Various modifications to these aspects will be readily apparent, and the generic principles defined herein may be applied to other aspects. Thus, the claims are not intended to be limited to the aspects shown herein, but is to be accorded the full scope consistent with the language claims, where reference to an element in the singular is not intended to mean "one and only one" unless specifically so stated, but rather "one or more." More particularly, for any of the one or more elements that element can be present in one, two, three, four, five, six, seven, eight, nine, ten or more. Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the subject technology.

A phrase, for example, an "aspect" does not imply that the aspect is essential to the subject technology or that the aspect applies to all configurations of the subject technology. A disclosure relating to an aspect may apply to all configurations, or one or more configurations. A phrase, for example, an aspect may refer to one or more aspects and vice versa. A phrase, for example, a "configuration" does not imply that such configuration is essential to the subject technology or that such configuration applies to all configurations of the subject technology. A disclosure relating to a configuration may apply to all configurations, or one or more configurations. A phrase, for example, a configuration may refer to one or more configurations and vice versa.

Those skilled in the art will understand the features and aspects of a suitable computing environment in which aspects of the disclosure may be implemented. Although not required, some of the embodiments of the claimed inventions may be described in the context of computer-executable instructions, such as program modules or engines, as described earlier, being executed by computers in networked environments. Such program modules are often reflected and illustrated by flow charts, sequence diagrams, exemplary screen displays, and other techniques used by those skilled in the art to communicate how to make and use such computer program modules. Generally, program modules include routines, programs, functions, objects, components, data structures, and application programming interface (API) calls to other computers whether local or remote that perform particular tasks or implement particular defined data types, within the computer. Computer-executable instructions, associated data structures and/or schemas, and program modules represent examples of the program code for executing steps of the methods disclosed herein. The particular sequence of such executable instructions or associated data structures represent examples of corresponding acts for implementing the functions described in such steps.

Those skilled in the art will also appreciate that the claimed and/or described systems and methods may be practiced in network computing environments with many types of computer system configurations, including personal computers, smartphones, tablets, hand-held devices, multi-processor systems, microprocessor-based or programmable consumer electronics, networked PCs, minicomputers, mainframe computers, and the like. Embodiments of the claimed invention are practiced in distributed computing environments where tasks are performed by local and remote processing devices that are linked (either by hard-wired links, wireless links, or by a combination of hardwired or wireless links) through a communications network. In a distributed computing environment, program modules may be located in both local and remote memory storage devices.

An exemplary system for implementing various aspects of the described operations, which is not illustrated, includes a computing device including a processing unit, a system memory, and a system bus that couples various system components including the system memory to the processing unit. The computer will typically include one or more data storage devices for reading data from and writing data to. The data storage devices provide nonvolatile storage of computer-executable instructions, data structures, program modules, and other data for the computer.

Computer program code that implements the functionality described herein typically comprises one or more program modules that may be stored on a data storage device. This program code, as is known to those skilled in the art, usually includes an operating system, one or more application programs, other program modules, and program data. A user may enter commands and information into the computer through keyboard, touch screen, pointing device, a script containing computer program code written in a scripting language or other input devices (not shown), such as a microphone, etc. These and other input devices are often connected to the processing unit through known electrical, optical, or wireless connections.

The computer that effects many aspects of the described processes will typically operate in a networked environment using logical connections to one or more remote computers or data sources, which are described further below. Remote computers may be another personal computer, a server, a router, a network PC, a peer device or other common network node, and typically include many or all of the elements described above relative to the main computer system in which the inventions are embodied. The logical connections between computers include a local area network (LAN), a wide area network (WAN), virtual networks (WAN or LAN), and wireless LANs (WLAN) that are presented here by way of example and not limitation. Such networking environments are commonplace in office-wide or enterprise-wide computer networks, intranets, and the Internet.

When used in a LAN or WLAN networking environment, a computer system implementing aspects of the invention is connected to the local network through a network interface or adapter. When used in a WAN or WLAN networking environment, the computer may include a modem, a wireless link, or other mechanisms for establishing communications over the wide area network, such as the Internet. In a networked environment, program modules depicted relative to the computer, or portions thereof, may be stored in a remote data storage device. It will be appreciated that the network connections described or shown are exemplary and other mechanisms of establishing communications over wide area networks or the Internet may be used.

While various aspects have been described in the context of a preferred embodiment, additional aspects, features, and methodologies of the claimed inventions will be readily discernible from the description herein, by those of ordinary skill in the art. Many embodiments and adaptations of the disclosure and claimed inventions other than those herein described, as well as many variations, modifications, and equivalent arrangements and methodologies, will be apparent from or reasonably suggested by the disclosure and the foregoing description thereof, without departing from the substance or scope of the claims. Furthermore, any sequence(s) and/or temporal order of steps of various processes described and claimed herein are those considered to be the best mode contemplated for carrying out the claimed inventions. It should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in a variety of different sequences and orders, while still falling within the scope of the claimed inventions. In addition, some steps may be carried out simultaneously, contemporaneously, or in synchronization with other steps.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility. It is therefore intended by the appended claims to cover any and all such applications, modifications and embodiments within the scope of the present invention.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application.

What is claimed is:

1. A computer-implemented method, comprising the steps of: measuring one or more baselines of neurophysiological data of a user with one or more sensors; calibrating one or more neurophysiological behavioral risk thresholds of the user using the one or more sensors based on the one or more baselines of neurophysiological data of the user; collecting one or more real-time neurophysiological data of the user with the one or more sensors while the user is experiencing a real-time relapse-inducing situation; upon determination that the one or more real-time neurophysiological data exceeds at least one of the one or more neurophysiological behavioral risk thresholds of the user, automatically providing one or more recovery cues to a device of the user for presentment to the user in real-time during the real-time relapse-inducing situation, wherein: the one or more recovery cues comprise an interactive automated chat; and prior to being provided to the device of the user, the one or more recovery cues were determined to demonstrate efficacy in reducing prior neurophysiological data of the user below the one or more neurophysiological behavioral risk thresholds while the user was being subjected to a prior relapse-inducing situation; measuring a response of the user to presentment of the one or more recovery cues; based on the response of the user, modifying an exposure frequency of the one or more recovery cues, following the presentment of the one or more recovery cues to the user, determining a rate of change of the one or more real-time neurophysiological data; and removing at least one of the one or more recovery cues from the device of the user based on a determination that the rate of change does not meet a predefined rate.

2. The method of claim 1, wherein the user suffers from a disease or disorder selected from a list comprising: addiction disorders, substance addiction, depression, post-traumatic stress disorder, anxiety disorders, phobias, and behavioral regulation disorders.

3. The method of claim 1, wherein the device of the user is selected from a list comprising: desktop computer, laptop computer, tablet computer, smartphone, smartwatch, wearable electronic device.

4. The method of claim 1, further comprising: after the presentment of the one or more recovery cues to the user, collecting second neurophysiological data; and determining an efficacy of the one or more recovery cues based at least in part on the one or more real-time neurophysiological data, the second neurophysiological data, and one or more predetermined threshold values associated with a predetermined situation that does not present a relapse risk.

5. The method of claim 4, further comprising, upon determination that the efficacy meets a predetermined efficacy threshold value of the one or more predetermined threshold values, prioritizing the one or more recovery cues for future presentment to the user.

6. The method of claim 4, further comprising, upon determination that the efficacy does not meet a predetermined efficacy threshold value of the one or more predetermined threshold values, removing the one or more recovery cues from the device of the user.

7. The method of claim 1, wherein the prior relapse-inducing situation is associated with substance use.

8. The method of claim 1, wherein the one or more recovery cues have personal meaning to the user.

9. The method of claim 1, wherein the one or more recovery cues were selected by the user before the user was subjected to the prior relapse-inducing situation.

10. A non-transitory, computer-readable medium comprising instructions that, when executed by a computer, cause the computer to: measure one or more baselines of neurophysiological data of a user with one or more sensors; calibrate one or more neurophysiological behavioral risk thresholds of the user using the one or more sensors based on the one or more baselines of neurophysiological data of the user; collect one or more real-time neurophysiological data of the user with the one or more sensors while the user is experiencing a real-time relapse-inducing situation; upon determination that the one or more real-time neurophysiological data exceeds at least one of the one or more neurophysiological behavioral risk thresholds of the user, automatically provide one or more recovery cues to an electronic computing device of the user for presentment to the user in real-time during the real-time relapse-inducing situation, wherein: the one or more recovery cues comprise an interactive automated chat; and prior to being provided to the device of the user, the one or more recovery cues were determined to demonstrate efficacy in reducing prior neurophysiological data of the user below the one or more neurophysiological behavioral risk thresholds while the user was being subjected to a prior relapse-inducing situation; measure a response of the user to presentment of the one or more recovery cues on the electronic computing device; based on the response of the user, modify an exposure frequency of the one or more recovery cues, following the presentment of the one or more recovery cues to the user, determine a rate of change of the one or more real-time neurophysiological data; and remove at least one of the one or more recovery cues from the electronic computing device of the user based on a determination that the rate of change does not meet a predefined rate.

11. The non-transitory, computer-readable medium of claim 10, wherein the user suffers from a disease or disorder selected from a list comprising: addiction disorders, substance addiction, depression, post-traumatic stress disorder, anxiety disorders, phobias, and behavioral regulation disorders.

12. The non-transitory, computer-readable medium of claim 10, wherein the instructions executed by the computer of measuring the one or more baselines of neurophysiological data of the user with one or more sensors and calibrating one or more neurophysiological behavioral risk thresholds of the user using the one or more sensors are performed in a virtual reality environment.

13. A system comprising: one or more sensors; one or more electronic computing devices; and a server, wherein the server comprises: one or more processors, and a memory comprising instructions that, when executed by the one or more processors, cause the one or more processors to: measure one or more baselines of neurophysiological data of a user with the one or more sensors; calibrate one or more neurophysiological behavioral risk thresholds of the user using the one or more sensors based on the one or more baselines of neurophysiological data of the user measure one or more real-time neurophysiological data of the user with the one or more sensors while the user is experiencing a real-time relapse-inducing situation; upon determination that the one or more real-time neurophysiological data exceeds at least one of the one or more neurophysiological behavioral risk thresholds of the user, automatically and in real-time provide one or more recovery cues to an electronic computing device of the one or more electronic computing devices of the user during the real-time relapse-inducing situation; wherein: the one or more recovery cues comprises an interactive automated chat; and prior to being provided to the one or more electronic computing devices of the user, the one or more recovery cues were determined to demonstrate efficacy in reducing prior neurophysiological data of the user below the one or more neurophysiological behavioral risk thresholds while the user was being subjected to a prior relapse-inducing situation; measure a response of the user to presentment of the one or more recovery cues on the one or more electronic computing devices of the user; based on the response of the user, modify an exposure frequency of the one or more recovery cues, following the presentment of the one or more recovery cues to the user, determine a rate of change of the one or more real-time neurophysiological data; and remove at least one of the one or more recovery cues from the electronic computing device of the one or more electronic computing devices of the user based on a determination that the rate of change does not meet a predefined rate.

14. The system of claim 13, wherein the user suffers from a disease or disorder selected from a list comprising: addiction disorders, substance addiction, depression, post-traumatic stress disorder, anxiety disorders, phobias, and behavioral regulation disorders.

15. The system of claim 13, wherein the instructions executed by the one or more processors of measuring the one or more baselines of neurophysiological data of the user with the one or more sensors and calibrating the one or more neurophysiological behavioral risk thresholds of the user using the one or more sensors are performed in a virtual reality environment.

16. The system of claim 13, wherein the electronic computing device of the user is selected from the list comprising: desktop computer, laptop computer, tablet computer, smartphone, smartwatch, wearable electronic device.

* * * * *